United States Patent
Fride et al.

(10) Patent No.: US 7,214,716 B2
(45) Date of Patent: May 8, 2007

(54) AGONISTS SPECIFIC FOR THE PERIPHERAL CANNABINOID RECEPTOR

(75) Inventors: Ester Fride, Efrat (IL); Aviva Breuer, Jerusalem (IL); Lumir Hanus, Jerusalem (IL); Susanna Tchilibon, Jerusalem (IL); Michal Horowitz, Jerusalem (IL); Raphael Mechoulam, Jerusalem (IL); Aaron Garzon, Rehovot (IL)

(73) Assignee: Yissum Research Development Co. of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 11/043,089

(22) Filed: Jan. 27, 2005

(65) Prior Publication Data

US 2005/0165118 A1 Jul. 28, 2005

Related U.S. Application Data

(60) Division of application No. 10/133,153, filed on Apr. 26, 2002, now Pat. No. 6,903,137, which is a continuation of application No. PCT/US00/29903, filed on Oct. 30, 2000, and a division of application No. 09/698,071, filed on Oct. 30, 2000, now Pat. No. 6,864,291.

(51) Int. Cl.
*A61K 31/075* (2006.01)
(52) U.S. Cl. .................................. 514/719; 514/729
(58) Field of Classification Search ................ 514/719, 514/729
See application file for complete search history.

(56) References Cited

U.S. PATENT DOCUMENTS

| | | | |
|---|---|---|---|
| 4,282,248 A | 8/1981 | Mechoulam et al. | 424/299 |
| 5,434,295 A | 7/1995 | Mechoulam et al. | 560/141 |
| 6,013,648 A | 1/2000 | Rinaldi et al. | 514/235.2 |
| 6,903,137 B2 * | 6/2005 | Fride et al. | 514/719 |

OTHER PUBLICATIONS

Calignano, A. et al., "Control of pain initiation by endogenous cannabinoids", Nature 394: 277-81, 1998.
Devane, W.A. et al., "Isolation and structure of a brain constituent that binds to the cannabinoid receptor", Science 258: 1946-9, 1992.
Devane, W.A. et al., "A novel probe for the cannabinoid receptor", J. Med. Chem. 35: 2065-9, 1992.
Fride, E. et al., "Pharmacological activity of the cannabinoid receptor agonist, anandamide, a brain constituent", Eur. J. Pharmacol. 231: 313-4, 1993.
Galve-Roperh, I. et al., "Anti-tumoral action of cannabinoids: involvement of sustained ceramide accumulation and extracellular signal-regulated kinase activation", Nature Medicine 6: 313-9, 2000.
Griffin, G. et al., "Evidence for the presence of $CB_2$-like cannabinoid receptors on peripheral nerve terminals", Eur. J. Pharmacol. 339: 53-61, 1997.
Hanus, L. et al., "HU-308: a specific agonist for $CB_2$, a peripheral cannabinoid receptor", Proc. Nat. Acad. Sci. USA 96: 14228-33, 1999.
Jaggar, S.I. et al., "The anti-hyperalgesic actions of the cannabinoid anandamide and the putative CB2 receptor agonist palmitoylethanolamide in visceral and somatic inflammatory pain", Pain 76: 189-99, 1998.
Martin, B.R. et al., "Behavioral, biochemical, and molecular modeling evaluations of cannabinoid analogs", Pharmacol. Biochem. Behavior 40: 471-8, 1991.
Mechoulam, R. et al., "Synthesis of the individual, pharmacologically distinct, enantiomers of a tetrahydrocannabinol derivative", Tetrahedron Asymmetry 1(5): 315-8, 1990.
Mechoulam, R. et al., "Identification of an endogenous 2-monoglyceride, present in canine gut, that binds to cannabinoid receptors", Biochem. Pharmacol. 50: 83-90, 1995.
Murthy, S.N.S. et al., "Treatment of dextran sulfate sodium-induced murine colitis by intracolonic cyclosporin", Dig. Dis. Sci. 38: 1722-34, 1993.
Tjølsen, A. et al., "The formalin test: an evaluation of the method", Pain 51: 5-17, 1992.
Young, J.M. et al., "The mouse ear inflammatory response to topical arachidonic acid", J. Invest. Dermatol. 82: 367-71, 1984.
Gareau et al., "Structure activity relationships of tetrahydrocannabinol analogues on human cannabinoid receptors," Bioorganic & Medicinal Chemistry Letters, vol. 6, No. 2, pp. 189-194 (1996).
Levin et al., "Structural features affecting chiral resolution of cannabimimetic enantiomers by amylose 3,5-dimethylphenylcarbamate chiral stationary phase," Chirality, vol. 7, No. 3, pp. 140-146 (1995).

* cited by examiner

*Primary Examiner*—Samuel Barts
(74) *Attorney, Agent, or Firm*—Winston & Strawn LLP

(57) ABSTRACT

The invention provides novel pharmaceutical compositions comprising as the active ingredient 4-phenyl pinene derivatives which are specific for the peripheral cannabinoid receptors. In particular, the compounds of the invention binds efficiently to CB2 but do not bind to CB1. The compounds show no activity in behavioral tests in mice which together have been shown to be specific for tetrahydrocannabinol (THC)- type activity in the central nervous system mediated by CB1 but reduce blood pressure, block intestinal motility, and elicit anti-inflammatory and peripheral analgetic activity. The invention also relates to methods of treating, preventing, or managing hypertension, inflammation, pain, gastrointestinal diseases, autoimmune diseases, and tumors with the compounds of the invention.

11 Claims, 9 Drawing Sheets

AGONISTS SPECIFIC FOR THE PERIPHERAL CANNABINOID RECEPTOR

CROSS-REFERENCE TO RELATED APPLICATIONS

This application is a division of application Ser. No. 10/133,153 filed Apr. 26, 2002 now U.S. Pat. No. 6,903,137, which is a continuation of International application no. PCT/US00/29903 filed Oct. 30, 2000, and a divisional of U.S. application Ser. No. 09/698,071, filed Oct. 30, 2000 now U.S. Pat. No. 6,864,291, each application being expressly incorporated herein by reference thereto.

FIELD OF THE INVENTION

The present invention relates to non-psychotropic cannabinoids that are specific agonists of the peripheral cannabinoid receptor CB2. More particularly, the invention relates to pharmaceutical compositions comprising 4-phenyl pinene derivatives which are specific CB2 agonists that are useful in preventing, treating, and managing hypertension, inflammation, pain, gastrointestinal disorders, autoimmune diseases and tumors.

BACKGROUND OF THE INVENTION

Mechoulam et al. have reported that two cannabinoid receptors have been identified: CB1, present in the central nervous system (CNS) and to a lesser extent in other tissues, and CB2 present outside the CNS, in peripheral organs including peripheral nerve terminals [Mechoulam et al., Proc. Nat. Acad. Sci., U.S., 96, 14228–14233]. *Cannabis sativa* preparations have been known as therapeutic agents against various diseases for millenia. The native active constituent, Delta 9-tetrahydrocannabinol (delta-9-THC) is prescribed today under the generic name Dronabinol, to treat vomiting and for enhancement of appetite, mainly in AIDS patients.

Separation between the therapeutically undesirable psychotropic effects from the clinically desirable ones, however, has not been reported with agonists that bind to cannabinoid receptors. THC, as well as the two major endogenous compounds identified so far that bind to the cannabinoid receptors, anandamide and 2-arachidonylglycerol (2-AG) produce most of their effects by binding to both the CB1 and CB2 cannabinoid receptors. The CB1 receptor is present in the CNS, and to a lesser extent in other tissues. The CB2 receptor is not present in the CNS, but mostly in peripheral tissue associated with immune functions, including macrophages and B cells, as well as in peripheral nerve terminals. While the effects mediated by CB1, mostly in the CNS, have been thoroughly investigated, those mediated by CB2 are not well defined.

Inhibition of gastrointestinal activity has been observed after administration of Delta 9-THC or of anandamide. This effect has been assumed to be CB1-mediated since the specific CB1 antagonist SR 141716A blocks the effect. Another report, however, suggests that inhibition of intestinal motility may also have a CB2-mediated component.

Cannabinoids are well known for their cardiovascular activity. Activation of peripheral CB1 receptors contributes to hemorrhagic and endotoxin-induced hypotension. Anandamide and 2-AG, produced by macrophages and platelets, respectively, may mediate this effect.

The hypotension in hemorrhaged rats was prevented by the CB1 antagonist SR 141716A. Recently the same group found that anandamide-induced mesenteric vasodilation is mediated by an endothelially located SR 141716A-sensitive "anandamide receptor," distinct from the CB1 cannabinoid receptor, and that activation of such a receptor by an endocannabinoid, possibly anandamide, contributes to endotoxin-induced mesenteric vasodilation in vivo. The highly potent synthetic cannabinoid HU-210, as well as 2-AG, had no mesenteric vasodilator activity. Furthermore it was shown that mesenteric vasodilation by anandamide apparently has 2 components, one mediated by a SR 141716-sensitive non-CB1 receptor (located on the endothelium) and the other by an SR 141716A-resistant direct action on vascular smooth muscle.

The production of 2-AG is enhanced in normal, but not in endothelium-denuded rat aorta on stimulation with carbachol, an acetylcholine receptor agonist. 2-AG potently reduces blood pressure in rats and may represent an endothelium-derived hypotensive factor.

Anandamide attenuates the early phase or the late phase of pain behavior produced by formalin-induced chemical damage. This effect is produced by interaction with CB1 (or CB1-like) receptors, located on peripheral endings of sensory neurons involved in pain transmission. Palmitylethanolamide, which like anandamide is present in the skin, also exhibits peripheral antinociceptive activity during the late phase of pain behavior. Palmitylethanolamide, however does not bind to either CB1 or CB2. Its analgetic activity is blocked by the specific CB2 antagonist SR 144528, though not by the specific CB1 antagonist SR 141716A. Hence a CB2-like receptor was postulated.

U.S. Pat. No. 5,434,295 discloses a family of novel 4-phenyl pinene derivatives, and teaches how to use those compounds in pharmaceutical compositions useful for treating various pathological conditions associated with damage to the central 30 nervous system. U.S. Pat. No. 4,282,248 discloses additional pinene derivatives. These patents do not mention that any of the compounds disclosed therein are selective for peripheral cannabinoid receptors.

Several synthetic cannabinoids have been shown to bind to the CB2 receptor with a higher affinity than to the CB1 receptor. Most of these compounds exhibit only modest selectivity. One of the described compounds, a classical THC-type cannabinoid, L-759,656, in which the phenolic group is blocked as a methyl ether, has a CB1/CB2 binding ratio >1000. The pharmacology of those known agonists has yet to be described.

Certain tumors, especially gliomas, express CB2 receptors. Guzman and coworkers have shown that delta -9-tetrahydrocannabinol and WIN-55,212-2, two non-selective cannabinoid agonists, induce the regression or eradication of malignant brain tumors in rats and mice [Guzman, et al., Nature Medicine 6,313-319, (2000)]. The rat glioma C6 expresses the CB2 receptor and, on the basis of studies with CB1 and CB2 selective antagonists, it has been proposed that activation of either of the two receptors may trigger apopotosis.

Thus, there is a need for selective peripheral cannabinoid receptors and particularly for specific agonists of the peripheral cannabinoid receptor CB2. The present invention now satisfies that need.

SUMMARY OF THE INVENTION

The present invention teaches how to isolate the effects mediated by peripheral cannabinoid receptors CB2 by providing specific CB2 agonists. The present invention also discloses a certain CB2 specific agonist which is capable of exerting its CB2 specific effects in vivo. Thus, the invention also enables new therapeutic entities to be formulated that include these specific CB2 agonists. The present invention further provides methods for preventing, treating, or managing diseases by administering to an animal in need thereof of a pharmaceutical composition containing as an active ingredient a therapeutically effective amount of a CB2 specific agonist.

The active ingredient of the pharmaceutical compositions according to the present invention is a compound of the general Formula 1:

Figure 1

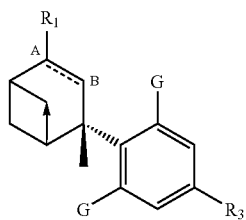

wherein A—B designates an optional double bond; $R_1$ designates a variety of organic moieties; G designates hydrogen, halogen or various ether groups; and $R_3$ designates various alkyl groups, ether groups, or combinations thereof.

In one aspect, the present invention utilizes compounds of Formula 1 as disclosed in U.S. Pat. No. 5,434,295, the teachings of which are expressly incorporated herein in their entirety by reference. All compounds of this invention have the (3S,4S) configuration and are essentially free of the (3R,4R) enantiomer.

In addition, certain compounds disclosed herein are novel and in themselves constitute an aspect of the present invention. These compounds include those in which G is hydrogen. Other preferred embodiments include compounds of Formula 1 wherein G is hydrogen or $OR_2$, and wherein $R_2$ is a lower alkyl group of one to five carbon atoms.

According to a more preferred embodiment, the synthesis and utility of a specific ligand, designated herein as HU-308, is disclosed along with its differential binding to CB-1 and CB-2, and its action on several in vivo assays, known to be affected by cannabinoids. HU-308 is a compound of the general Formula 1 wherein $R_1$, is $CH_2OH$, G is methoxy, and $R_3$ is 1,1 dimethylheptyl. HU-308, however, reduces blood pressure, blocks defecation, and elicits anti-inflammatory and peripheral analgetic activity. The hypotensive, anti-inflammatory, peripheral analgetic activity and gastrointestinal effects produced by HU-308 are blocked by the CB2 antagonist SR 144528, but not by the CB1 antagonist SR 141716A.

Accordingly, the present invention provides novel non-psychotropic cannabinoids and provides new therapies for hypertension, inflammation, pain, gastrointestinal diseases, autoimmune diseases, and tumors.

BRIEF DESCRIPTION OF THE DRAWINGS

Preferred features of the invention can be understood from a review of the following detailed description and drawing, wherein.

DETAILED DESCRIPTION OF THE PREFERRED EMBODIMENTS

Figure 1:
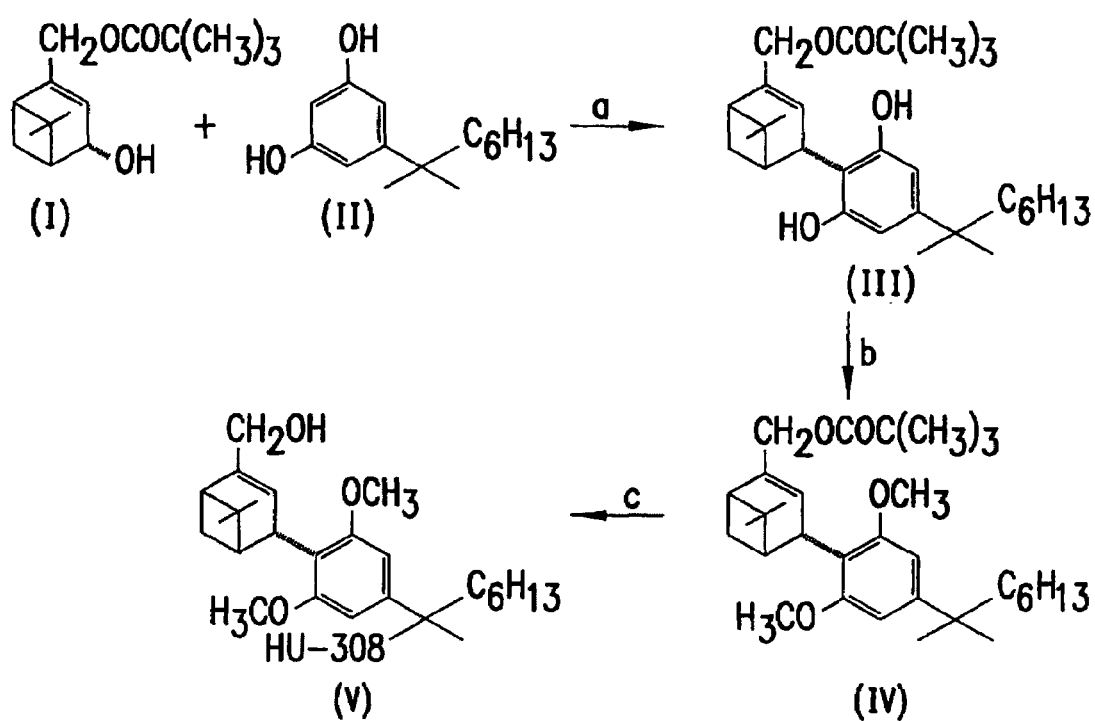
FIG. 1 depicts a reaction scheme for synthesizing HU-308.

Selective agonists for specific receptors are of interest and importance since biochemical and pharmacological investigations of individual receptors may lead to the development of new drugs or drug leads. The present invention provides novel medicinal uses for the pinene derivatives of general Formula 1. These compounds have unexpectedly been shown to be CB2 specific agonists. Specifically, the methods involve the use of appropriately formulated pharmaceutical compositions with CB2 agonist activity that contain as their active ingredient a compound of the Formula 1:

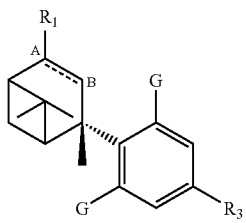

wherein the dotted line A—B indicates an optional bond and the substituents $R_1$, G, and $R_3$ are defined as follows:

R1 is (a) —R'N(R")$_2$ wherein R' is $C_1$–$C_5$ straight or branched chain alkyl and each R", which may be the same or different, is hydrogen or $C_1$–$C_5$ straight or branched chain alkyl optionally containing a terminal —OR'" or —OC(O)R'" moiety wherein R'" is hydrogen or $C_1$–$C_5$ straight or branched chain alkyl, (b) —Q wherein Q is a heterocyclic moiety having a labile hydrogen atom so that said moiety acts as a carboxylic acid analogue, (c) —R'X wherein R' is $C_1$–$C_5$ straight or branched chain alkyl and X is halogen, (d) —R'C(O)N(R")$_2$ wherein R' is a direct bond or $C_1$–$C_5$ straight or branched chain alkyl and each R'", which may be the same or different, is hydrogen or $C_1$–$C_5$ straight or branched chain alkyl optionally containing a terminal —OR'" or —OC(O)R'" moiety wherein R'" is hydrogen or $C_1$–$C_5$ straight or branched chain alkyl, (e) —R'C(O)OR" wherein R' is a direct bond or $C_1$–$C_5$ straight or branched chain alkyl and R" is hydrogen or $C_1$–$C_5$ straight or branched chain alkyl optionally containing a terminal —OR'" or —OC(O)R'" moiety wherein R'" is hydrogen or $C_1$–$C_5$ straight or branched chain alkyl, (f) —R' wherein R' is $C_1$–$C_5$ straight or branched chain alkyl, or (g) —R'OR'" wherein R' is $C_1$–$C_5$ straight or branched chain alkyl and R'" is hydrogen or $C_1$–$C_5$ alkyl;

G is hydrogen, halogen, or —OR$_2$ wherein R$_2$ is hydrogen or $C_1$–$C_5$ alkyl optionally containing a terminal —OR'", —OC(O)R'", —C(O)OR'", or —C(O)R'" moiety wherein R'" is hydrogen or $C_1$–$C_5$ alkyl; and R$_3$ is (a) $C_1$–$C_{12}$ straight or branched chain alkyl, (b) —OR"", in which R"" is a straight chain or branched $C_2$–$C_9$ alkyl which may be substituted at the terminal carbon atom by a phenyl group, or (c) —(CH$_2$)$_n$OR'" wherein n is an integer of 1 to 7 and R'" is hydrogen or $C_1$–$C_5$ alkyl.

The compounds according to Formula 2 have the (3S,4S) configuration and are essentially free of the (3R,4R) enantiomer.

As noted above, certain compounds of the above formula, i.e., those wherein G is hydrogen, are novel and in themselves constitute a preferred aspect of the invention.

The synthesis and use of a new type of CB2 specific agonist, having the general Formula 1, as defined above, is now described. The principles of the invention are exemplified herein by the currently preferred compound of Formula 1, HU-308, which can be synthesized as described in FIG. 1.

Figure 2:
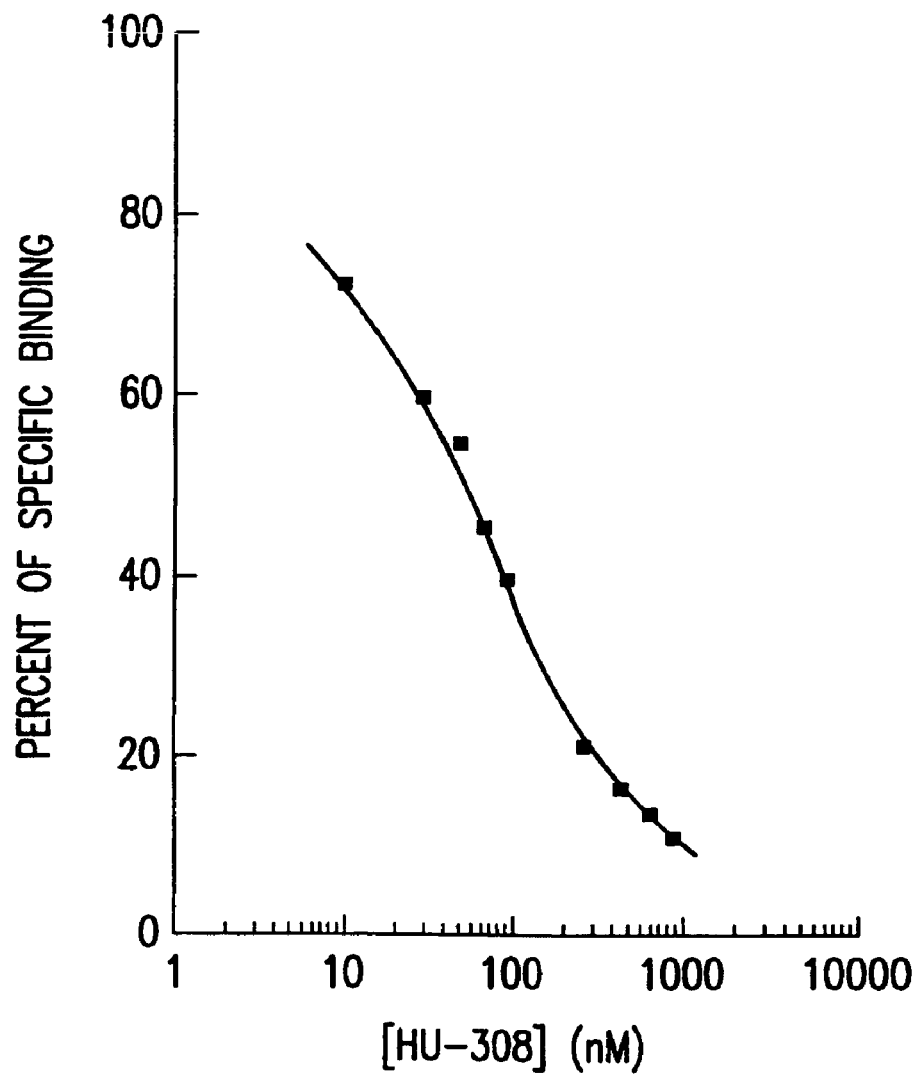
FIG. 2 depicts binding of HU-308 to the CB2 cannabinoid receptor measured by competitive inhibition of [$_3$H]HU-243 in COS-7 cells transfected with plasmids containing the CB2 receptor gene.
Figure 3A:
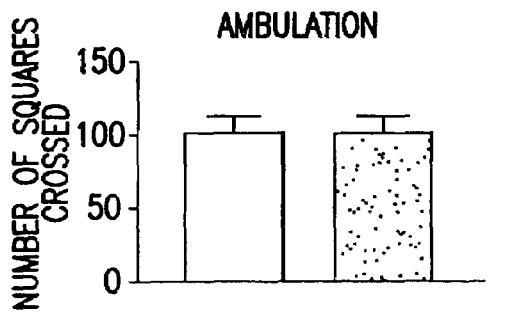
FIG. 3 depicts the effect of of HU-308 on female C57/BL6 mice tested, 2.5 hrs after i.p. injection of HU-308 (40 mg/kg) for: (a) ambulation; (b) rearing in open field; (c) immobility; (d) hypothermia; and (e) analgesia on a hot plate. Open bars represent mice treated with the vehicle and closed bars represent mice treated with HU-308 (50 mg/kg)
Figure 3B:
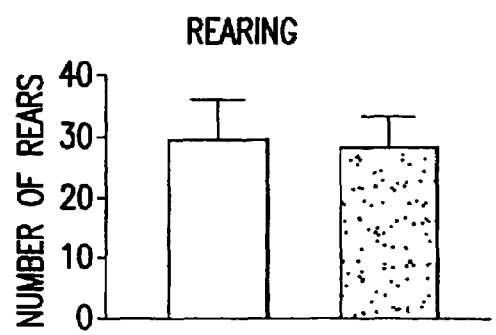
Figure 3C:
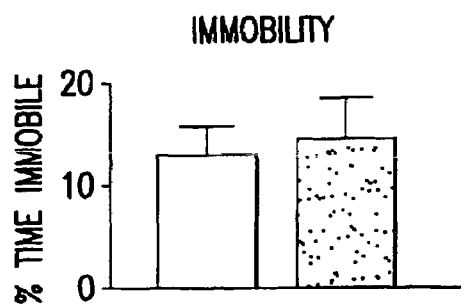
Figure 3D:
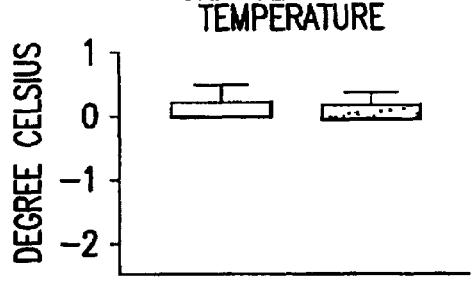
Figure 3E:
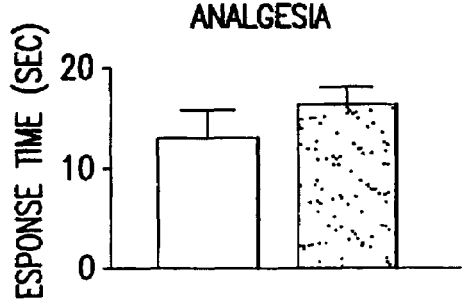

FIG. 2 shows that HU-308 binds to the CB2 cannabinoid receptor. HU-308 binds to the CB2 cannabinoid receptor with a Ki=22.7±3.9 nM, as measured by competitive inhibition of [$^3$H]HU-243 in COS-7 cells transfected with plasmids containing the CB2 receptor gene, as described in Mechoulam, R., Ben-Shabat, S., Hanus, L., Ligumsky, M., Kaminski, N. E., Schatz, A. R., Gopher, A., Almog, S., Martin, B. R., Compton, D. R., Pertwee, R. G., Griffin, G., Bayewitch, M., Barg, J. & Vogel, Z. (1995) Biochem. Pharmacol. 50, 83–90. HU-308, however does not bind to CBI (Ki>10 mM). This difference in binding is reflected in the results of the pharmacological assays. FIG. 3 shows that when female C57/BL6 mice are administered high a dose of HU-308 (40 mg/kg) by i.p. injection there is no decrease in their activity in an open field trial, no catalepsy, no reduction in body temperature, and no analgesia on a hot plate (hereinafter referred to as the tetrad of assays) when tested 10 min (data not shown), 30 min (data not shown), or 150 min after i.p. administration. Such effects are considered to be mediated by the CBI receptor.

Figure 4:
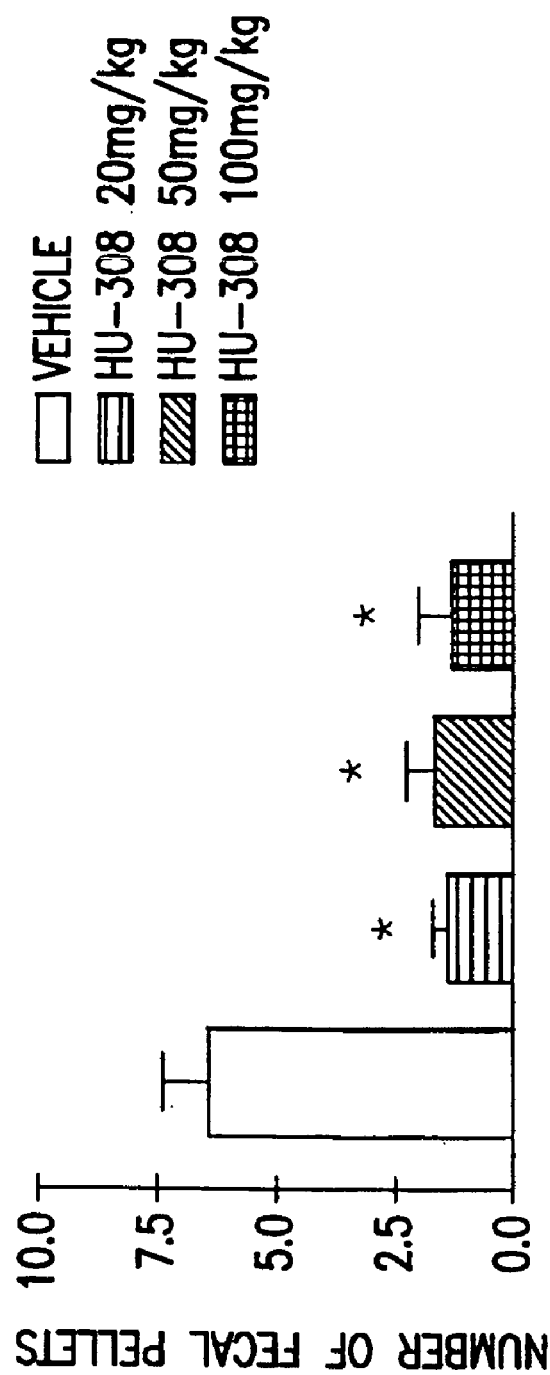
FIG. 4 depicts intestinal immotility in female Sabra mice as measured by the number of fecal pellets voided in a two hr period after HU-308 administration following i.p. injection of vehicle or HU-308 at 20, 50, or 100 mg/kg.

HU-308 also caused complete inhibition of intestinal mobility in mice at a dose of 20 mg/kg. FIG. 4 shows the effect the number of fecal pellets voided over 2 hrs after i.p. administration of HU-308 (20, 50, or 100 mg/kg) to female Sabra mice. Intestinal motility was assessed every 15 min (over a 2 hr period) by the cumulative number of fecal pellets voided in a two hour period after separating the mice into individual cages. After 75 min, mice which had received 100 mg/kg had voided significantly fewer boli than controls. By 90 min all treated groups differed from controls. Hence, this gastrointestinal effect may be mediated, at least in part, by the peripheral CB2 receptor. Indeed, administration of the CB2 antagonist SR144528 in part blocked this effect.

Figure 5:
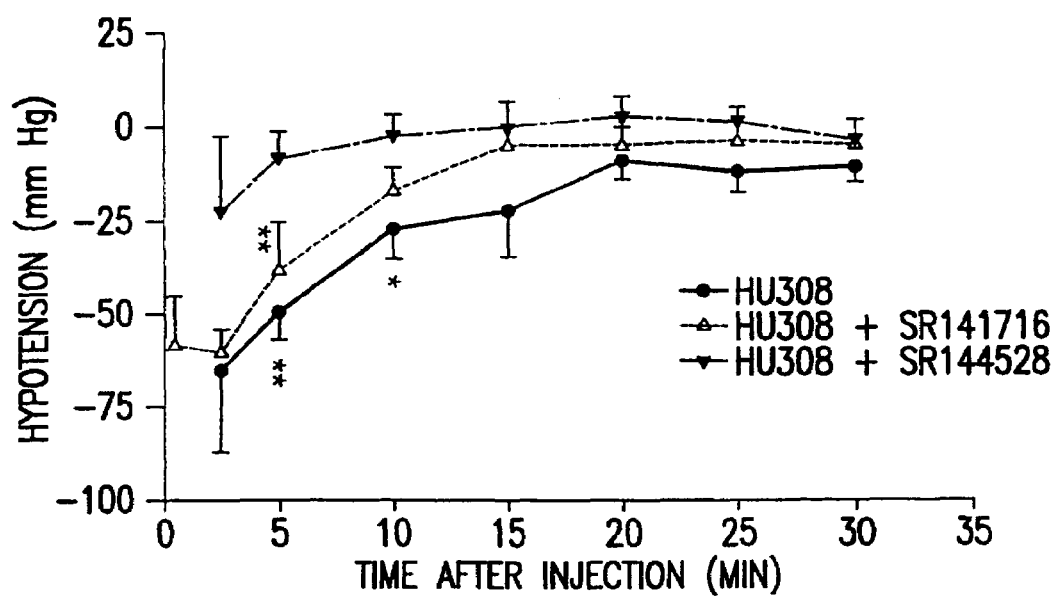
FIG. 5 depicts the hypotensive effects of HU-308, HU-308 and SR141716 (3 mg/kg), and HU-308 and SR144528 (1 mg/kg) in anesthetized rats.

HU-308 has been found to reduce blood pressure when administered to rats. FIG. 5 shows that HU-308 lowers blood pressure in anesthetized cannulated rats. Baseline blood pressure was recorded before administering HU-308. HU-308 was administered by i.v. at 30 mg/kg (lower doses did not have a significant effect). This cardiovascular effect is blocked by the CB2 antagonist SR 144528, but not by the CB1 antagonist SR 141716A. The antagonists SR141716A (3 mg/kg), or SR144528 (1 mg/kg) were injected 5 min prior to HU-308. An (*) in FIG. 5 denotes a value significantly different from the baseline value of controls (p<0.05).

Apparently the hypotensive effect caused by HU-308 is produced through a mechanism that differs from the previously described CB1-mediated (or the "anandamide receptor"-mediated) hypotension produced by endocannabinoids. This unexpected observation serves as a starting point for the development of novel hypotensive drugs, since HU-308 causes no psychotropic effects, as established by the lack of effect in the tetrad of assays described above, and therefore should not cause major undesirable effects in humans, because most cannabinoids do not produce significant side effects other than the psychotropic ones.

Figure 6A:
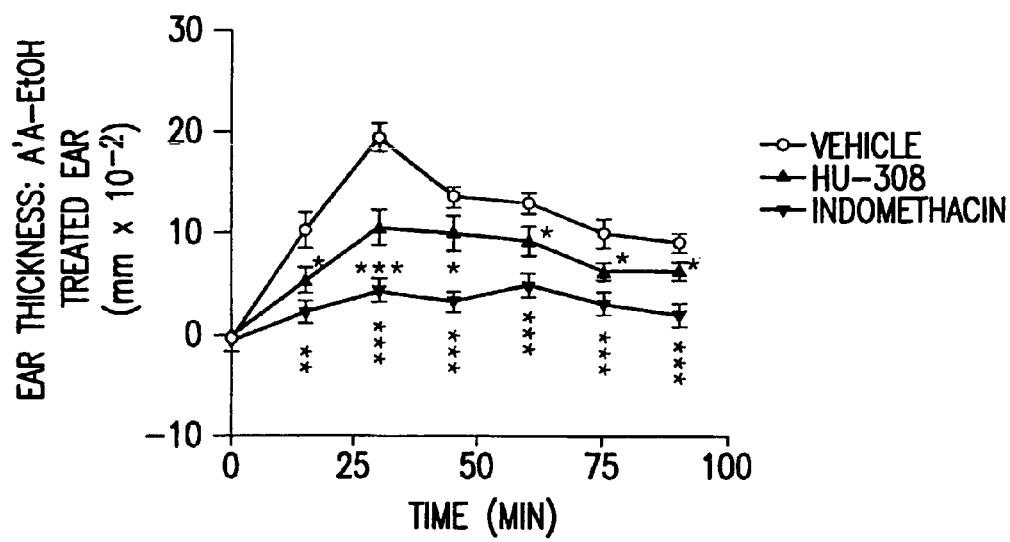
FIG. 6a is a time graph depicting the effects of HU-308 (50 mg/kg) and indomethacin (20 mg/kg) on arachidonic acid (A'A) induced swelling of the ear in female Sabra mice treated with 4.5 mg A'A (in 5 ml EtOH) dispersed on the inner surface of one of the ears as measured by the difference between the A'A treated ear and the EtOH treated ear every 15 min after A'A application for 90 min.
Figure 6B:
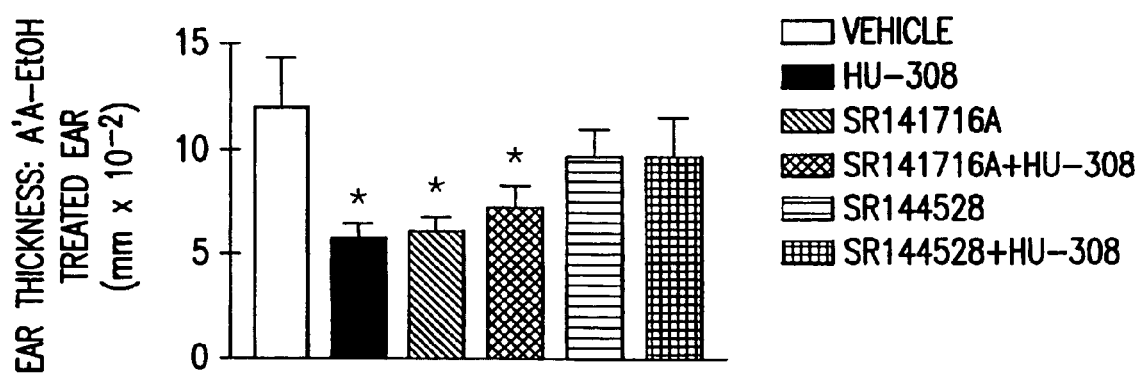
FIG. 6b is a bar graph depicting the effects of the CB1 receptor antagonist (SR141716A, 5 mg/kg) and the CB2 receptor antagonists (SR144528, 1 mg/kg) on the anti-inflammatory effect of HU-308 on arachidonic acid (A'A) induced swelling of the ear in female Sabra mice treated with 4.5 mg A'A (in 5 ml EtOH) dispersed on the inner surface of one of the ears as measured by the difference between the A'A treated ear and the EtOH treated ear.

HU-308 and indomethacin injected between 30 and 90 min before application of arachidonic acid, induced significant reduction of arachidonic acid-induced ear swelling at doses of 50 and 20 mg/kg, respectively. FIG. 6 shows the effect of HU-308 and indomethacin on arachidonic acid (A'A)-induced swelling of the ear in female Sabra mice treated with 4.5 mg A'A (in 5 ml EtOH) dispersed on the inner surface of one of the ears. The other ear was treated with 5 ml of EtOH and served as a control. Ear swelling was assessed by measuring ear thickness with a dial thickness gauge (Mitutoyo, Japan) just before treatment and every 15 min after A'A application for 90 min. Vehicle, HU-308 (50 mg/kg) or indomethacin (20 mg/kg) were injected i.p. 60 min before A'A application (injection of HU-308 30 or 90 min before A'A yielded similar results). Curve "a" is a time curve and illustrates that peak swelling of the ear is achieved about 30 min after A'A application. Curve "b" shows the effects of CB1 and CB2 receptor antagonists on the anti-inflammatory effect of HU-308. The CB1 antagonist (SR141716A, 5 mg/kg) or the CB2 receptor antagonist (SR144528, 1 mg/kg) were injected i.p. HU-308 was then administered (50 mg/kg i.p.) 60 min later and A'A was administered 50 min after HU-308. The results are presented as the difference between the A'A treated ear and the EtOH treated ear. N=5 for each treatment group. A (*) denotes a value significantly different from vehicle-treated mice (p<005), a () denotes a value significantly different from vehicle-treated mice (p<0.01), and a (*) denotes a value significantly different from vehicle-treated mice (p<0.001).

The results in FIG. 6 show that the anti-inflammatory effect produced by indomethacin was greater than that produced by HU-308. The CB1 antagonist SR 141716A (5 mg/kg) administered 15 min before HU-308, did not prevent the anti-inflammatory effect of HU-308. Rather, SR 141716A by itself reduced arachidonic acid-induced ear swelling. FIG. 6 also shows that the CB2 receptor antagonist SR 144528 (0.5 mg/kg) did not by itself induce an anti-inflammatory effect but reduced the anti-inflammatory effect of HU-308.

Figure 7:
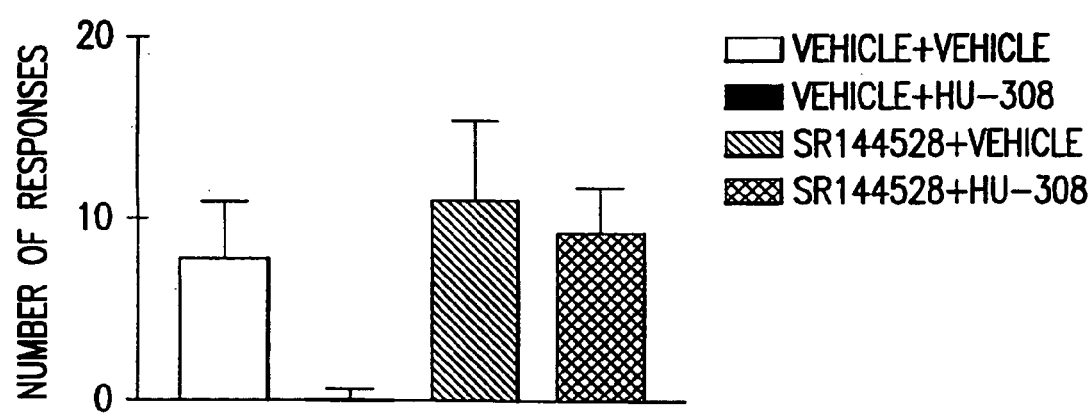
FIG. 7 is a bar graph depicting the effect of HU-308 and HU-308 plus SR144528 on formalin-induced peripheral pain in mice 30 minutes after injecting formalin into the hindpaw as measured by the total number of licks of the injected hindpaw recorded for the duration of one hour.

HU-308 also reduced peripheral pain during the late phase of pain behavior. FIG. 7 shows the effects of HU-308 without SR144528 on formalin-induced peripheral pain. Vehicle or SR144528 was injected 15 min before an injection of vehicle or HU-308 (50 mg/kg, i.p.). Ninety min after the injection of HU-308 formalin was injected subcutaneously into the foot. Pain was assessed as the total number of licks of the injected hindpaw recorded for the duration of one hr. Early (5 min) and late (25–60 min) phase pain were observed as described in Calignano, A., La Rana, G., Giuffrida, A. & Piomelli, D. (1998) Nature (London) 394, 277–280. HU-308-induced effects were only observed during the late phase. Therefore, the only data presented is data collected at 30 min after formalin injection. The results show that HU-308 reduced peripheral pain during the late phase of pain behavior and that this effect was prevented by SR 144528, the CB2 antagonist, but not by SR 141716A, the CB1 antagonist. HU-308 apparently acts through the CB2 receptor as it binds to CB2 but not to CB1. This observation is in agreement with the recent detection by Griffin et al. of CB2 receptors on peripheral nerve terminals [Griffin, G., Fernando, S. R., Ross, R. A., McKay, N. G., Ashford, M. L, J., Shire, D., Huffman, J. W., Yu, S., Lainton, J. A. H. & Pertwee, R. G. (1997) Eur. J. Pharmacol. 339, 53–61]. Whatever the exact mechanism of the activity of HU-308 on pain transmission, our results indicate that cannabinoids may serve as peripheral analgetics that have no central effects.

In summary, HU-308 does not bind to CB1 (Ki>10 mM), but efficiently binds to CB2 (Ki=22.7±3.9 nM). It shows no activity in a tetrad of behavioral tests in mice, which together have been shown to be specific for THC-type activity in the CNS. HU-308 reduces blood pressure, blocks defecation, and elicits anti-inflammatory and peripheral analgetic activity. The hypotension, anti-inflammatory, peripheral analgetic activity, and inhibition of gastrointestinal motility produced by HU-308 are blocked by the CB2 antagonist SR 144528, but not by the CBI antagonist SR 141716A.

These exemplary results, which are to be construed in a non-limiting manner, demonstrate the feasibility of novel non-psychotropic cannabinoids that may be used to treat hypertension, inflammation, pain, and gastrointestinal disorders. Indeed, the compositions of the invention are of special value in preventing, treating, and managing hypertension, inflammation, peripheral pain, and gastrointestinal disorders. The compositions of the invention also have utility in treating autoimmune diseases including, but not limited to, multiple sclerosis and arthritis and in treating tumors that express CB2 receptors, in particular gliomas that express CB2 receptors. Killing brain tumor cells with a CB2 selective agonist could allow tumor management without inducing undesired psychotropic side effects. Thus, the present invention provides methods for treating, preventing, and managing various pathological conditions including hypertension, inflammation, peripheral pain, gastrointestinal disorders, autoimmune diseases, and tumors.

The compounds are administered for the above defined purposes in conventional pharmaceutical forms, with the required solvents, diluents, excipients, etc. to produce a physiologically acceptable formulation. They can be administered by any of the conventional routes of administration.

Pharmaceutical compositions in which the compounds of the above formula are the active ingredient may be prepared in a variety of forms and dosages. Methods for preparing such compositions are readily known to those of ordinary skill in the art. Thus, the compounds may be formulated with a pharmaceutically acceptable diluent or carrier in accordance with standard procedures. For example, a diluent may be chosen that is an aqueous cosolvent solution comprising a pharmaceutically acceptable cosolvent, a micellar or emulsion solution prepared with natural or synthetic ionic or nonionic surfactants, or a combination of such cosolvent and micellar or emulsion solutions. A carrier consisting essentially of a solution of ethanol, a surfactant, and water may be used, or a carrier may be selected that consists essentially of an emulsion comprising triglycerides, lecithin, glycerol, an emulsifier, an antioxidant, and water. Prior to their use as medicaments, the pharmaceutical compositions will generally be formulated in unit dosage forms. Daily dosages of the compound for humans typically range from about 0.1 to 50 mg/kg, and preferably from about 1 to 20 mg/kg.

It will be appreciated that the most appropriate administration of the pharmaceutical compositions of the present invention will depend on the type of injury or disease being treated.

EXAMPLES

The principles of the present invention will be more fully understood in the following examples, which are to be construed in a non-limiting manner.

Example 1

Synthesis of (+)-(1-α-H,4-(3-H,5a-H)-4-[2,6-dihydroxy-4-(1,1-dimethylheptyl)phenyl]-6.6-dimethylbicyclo[13.1.1]hept-2-ene-2-2-carbinolpivalate (III)

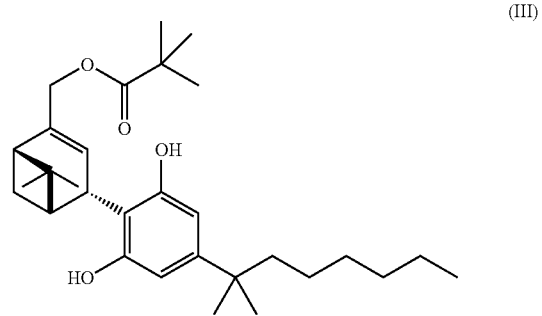

(III)

To a well stirred solution of 4-hydroxymyrtenyl pivalate (14.75 g, 40 mmol) and dimethylheptyl resorcinol (9.52 g, 40.3 mmol) in anhydrous dichloromethane (200 ml), was added p-toluenesulfonic acid anhydrous (1.5 g) in one portion. The reaction mixture was stirred at room temperature for one hour. TLC analysis indicated complete disappearance of the starting material. The reaction mixture was diluted with dichloromethane (200 mL) followed by 200 ml of a saturated aq. NaHCO$_3$ solution. The aqueous layer was separated and extracted with dichloromethane (2×200 mL) and the organic solutions combined. The combined organic solutions were washed twice with 150 mL of aq. NaHCO$_3$ solution and twice with 200 mL of brine. The organic layer was dried (Na$_2$SO$_4$), filtered, and evaporated to afford 23.54 g of crude material. The crude material was purified by flash chromatography on silica gel using 3% ethyl acetate/petroleum ether as the eluent to afford 11.2 g of pure material (III).

Example 2

Synthesis of 5-a-H-4-[2,6-dimethoxy-4-(1,1-dimethylheptyl)phenyl]-6,6-dimethylbicycloj3.1.1]kept-2-ene-2-carbinolpivalate (IV)

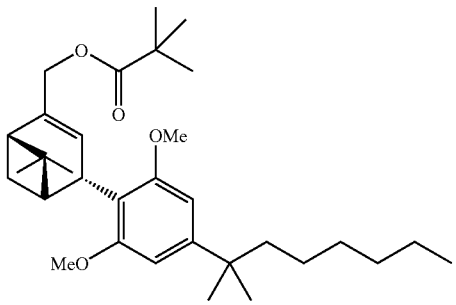

(IV)

To a well stirred suspension of (III) (10.81 g, 23 mmol) and potassium carbonate (12.84 g, 92 mmol) in anhydrous DMF (80 mL) was added, in one portion, methyl iodide (30 mL, 0.46 mol). The reaction mixture was stirred at room temperature under a nitrogen atmosphere for 3 days. HPLC analysis (80% acetonitrile, 20% water) showed the presence of 17% starting material, 39% of product, and 27% of the monomethylated product (VI, depicted below).

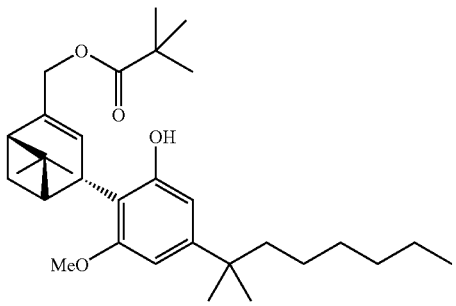

(VI)

An additional amount of potassium carbonate (12.93 g) and methyl iodide (20 mL) were added to the reaction mixture. The reaction was stopped after 2 hours and diluted with 250 mL of ether followed by 200 mL of water. The aqueous layer was extracted with ether (3×200 mL) and the combined organic layers washed with water (4×250 mL), dried (Na$_2$SO$_4$), filtered, and evaporated under reduced pressure to afford 11.15 g of crude material. The crude material was purified on silica gel by flash chromatography using 3% ether/petroleum ether as the eluent to provide 5.27 g of pure (V) and 1.7 g of pure (VI).

Example 3

Synthesis of (+)-(1-a-H,-(3-H,5-a-H)-4-(2,6-dimethoxy-4-(1,1-dimethylheptyl)phenyl]-6,6-dimethylbicycloj3.1.1]hept-2-ene-2-carbinol (HU-308) (V)

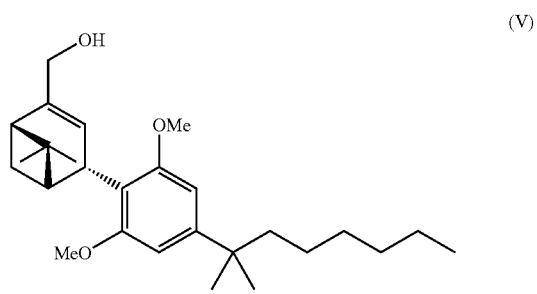

(V)

The starting materials for the synthesis of HU-308, 4-hydroxy-myrtenyl pivalate (I) and 5-(1,1-dimethylheptyl)-resorcinol (II), and the intermediate (III) in the synthesis of HU-308 were prepared as previously reported [Mechoulam, R., Lander, N., Breuer, A. & Zahalka, J. (1990) Tetrahedron: Asymmetry 1,315-319] and as described above. The synthesis of HU-308 is described in FIG. 1. In FIG. 1 "a" is dry p-toluenesulfonic acid in methylene chloride; "b" is potassium carbonate, methanol; and "c" is lithium aluminum hydride.

A solution of compound IV (5.076 g, 10.2 mmol) in freshly distilled anhydrous tetrahydrofuran (25 mL), was cooled to −40° C. Lithium aluminum hydride (1N in THF, 12 mL) was added dropwise to the cold solution. The reaction mixture was stirred at −40° C. for 10 min and then at room temperature for 30 min. TLC analysis indicated complete disappearance of compound (IV). The reaction mixture was cooled to −40° C. and 20 mL of ethyl acetate was added followed by 40 mL of a saturated aqueous MgSO$_4$ solution. The layers were separated and the aqueous layer was extracted with ethyl acetate (3×50 ml) and the combined organic layers were washed with brine (2×100 ml), dried (Na$_2$SO$_4$), filtered, and the solvent removed by evaporation to afford an oil which was lyophilized to afford 4.22 g of pure (V).

HU-308 has a melting point of 50° C. and $[\alpha]^D$=+127° C. (c=2.87 mg/cc CHCl$_3$). The structure of HU-308 was confirmed by $^1$H NMR, GC-MS and High Resolution Mass Spectroscopy (HRMS). NMR, 300 MHz, (CDCl$_3$): 6.45 (2H, s, aromatic), 5.7 (1H, olefinic), 4.12 (2H, CH$_3$O—), 4.01 (1H, benzylic), 3.7 (6H, OCH$_3$). HRMS calculated for C$_{27}$H$_{42}$O$_3$, 414.6287, found 414.3114.

Example 4

Synthesis of (+1-(1-a-H 4-[3-H.5-a-H1-4-[2,6-methoxy-hydroxy-4-(I,1-dimethylheptyl)phenyl]-6,6-dimethylbicyclo[3.1.1]hept-2-ene-2-carbinol (VII)

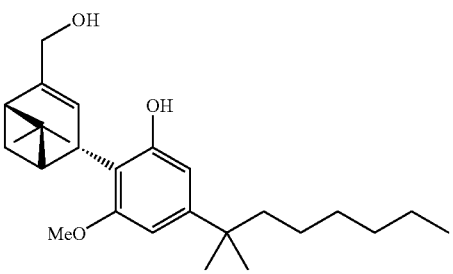

(VII)

A solution of compound VI (5.076 g, 10.2 mmol) in freshly distilled anhydrous tetrahydrofuran (25 mL), was cooled to −40° C. Lithium aluminum hydride (1N in THF, 12 mL) was added dropwise to the cold solution. The reaction mixture was stirred at −40° C. for 10 min and then at room temperature for 30 min. TLC analysis indicated complete disappearance of the starting material. The reaction mixture was cooled to −40° C. and 20 mL of ethyl acetate was added followed by 40 mL of a saturated aqueous $MgSO_4$ solution. The layers were separated and the aqueous layer was extracted with ethyl acetate (3×50 ml) and the combined organic layers were washed with brine (2×100 ml), dried ($Na_2SO_4$), filtered, and the solvent removed by evaporation to afford an oil which was lyophilized to afford 4.22 g of pure (VII).

Example 5

Synthesis of (+)-(1-a-H,4-(3-H 5-a-H)$_4$-j2 6-di(di-terbutylmethylsilyloxy)-4-(1 1-dimethylheptyl)phenyl]-6 6-dimethylbicyclo f3.1.11hept-2-ene-2-carbinolpivalate (VIII)

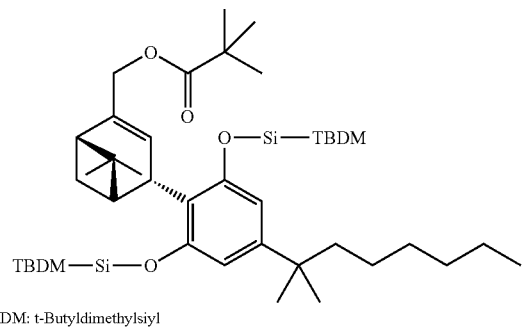

(VIII)

TBDM: t-Butyldimethylsiyl

The reaction was performed under a nitrogen atmosphere. To a well stirred solution of compound III (5.23 g, 11.1 mmol) and t-butyldimethylsilyl chloride (9.1088 g, 133.3 mmol) in dry THF (60 mL) was added imidazole (10.20 g, 66.76 mmol). The reaction mixture was stirred at room temperature overnight. The reaction was stopped by the addition of water (100 ml) and the aqueous solution was extracted with ether (3×150 ml). The organic layers were combined and washed with water (4×150 ml). The combined organic layers were dried ($Na_2SO_4$), filtered, and evaporated, under reduced pressure to provide 7.89 g of pure (VIII).

Example 6

Synthesis of (+)-(1-a-H 4-P-H S-a-H)-4-[2 6-di(di-tertbutylmethylsilyloxy)-4-dimethylheptyl)phenyl-6 6-dimethylbicyclo[3.1.1]hept-2-ene-2-carbinol (IX)

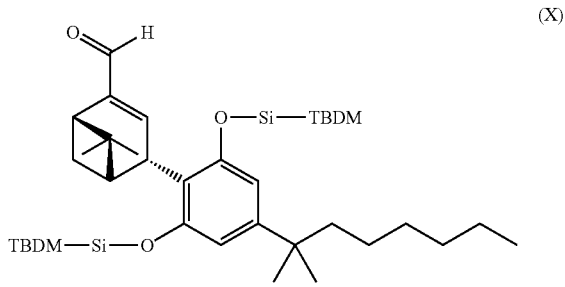

(X)

Compound VII (6.94 g, 10 mmol) was dissolved in freshly distilled dry THF (50 mL) and the solution cooled to −40° C. Lithium aluminum hydride (1N in THF, 12 mL) was added dropwise to the cooled solution. The cooling bath was removed and the reaction was allowed to stir at room temperature for 30 min. TLC analysis indicated complete disappearance of the starting material. The reaction mixture was cooled to −40° C. and 100 mL of ethyl acetate was added followed by 40 mL of a saturated aqueous $MgSO_4$ solution. The layers were separated and the aqueous layer was extracted with ethyl acetate (3×50 ml). The combined organic layers were washed with brine (2×100 ml), dried ($Na_2SO_4$), filtered, and the solvent removed by evaporation to afford an oil which was lyophilized to afford 4.54 g of pure (IX).

Example 7

Synthesis of (+)-(1-a-H,4-(3-H,5-a-H)-4-C2,6-di(di-tertbutylmethylsilyloxy) (1 1-dimethylheptyl).phenyl]-6,6-dimethylbicyclo[3.1.1]hept-2-ene-2-carboxaldehyde (X)

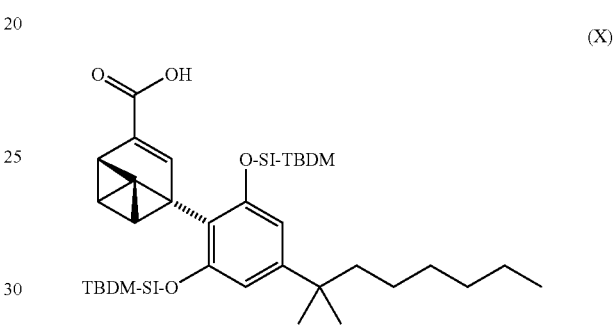

(X)

To a well stirred solution of compound IX (2.59 g, 4.23 mmol) in anhydrous dichloromethane (30 mL) was added pyridinium dichromate (3.22 g, 8.46 mmol) and the reaction mixture stirred at room temperature for 30 min. TLC analysis indicated complete disappearance of the starting material. The reaction mixture was diluted with water (300 ml) and the aqueous layer extracted with dichloromethane (3×200 ml). The organic layers were combined, washed with water (4×2590 ml), dried ($Na_2SO_4$), filtered through celite, and the solvent removed by evaporation to afford 2.5 g of crude material. The crude material was purified by flash chromatography on silica gel using 3% ether/petroleum ether as the eluent to afford 1.81 g of pure (X).

Example 8

Synthesis of (+)-(1-a-H,4,(3-H,5-a-H)-4-[2,6-di di-tertbutylmethylsilyloxy)-4-(1,1-dimethylheptyl)phenyl]-6 6-dimethylbicyclo[3.1.1)hept-2-ene-2-carboxylic Acid (XI)

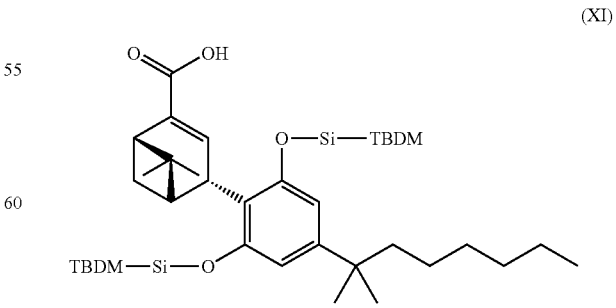

(XI)

To a well stirred solution of compound X (13.6 g, 22.28 mmol) in t-BuOH (120 mL) was added in small portions 2-methyl-2-butene (60 ml), a saturated aqueous solution of NaH$_2$PO$_4$ (30 ml), and sodium chlorite (11.10 g, 122.2 mmol). The reaction mixture was stirred at room temperature overnight and the reaction stopped by the addition of 100 mL of water. The aqueous layer was extracted with ethyl acetate (3×250 ml) and the organic layer was washed with water (3×300 ml). The combined organic layers were dried (Na$_2$SO$_4$), filtered, and evaporated under reduced pressure. The resulting residue (15 g) was purified by flash chromatography on silica gel using a gradient from 5% ethyl acetate/petroleum ether up to 20% ethyl acetate/petroleum ether to afford 13.49 g of (XI) (yield 96%).

Example 9

Synthesis of (+)-(1-a-H 4-P-H 5a-H)-4-(2,6-dihydroxy-4-(1,1-dimethylheptyl)phenyl-6-dimethylbicyclo[3.1.1]hept-2-ene-2-carboxylic Acid (XII)

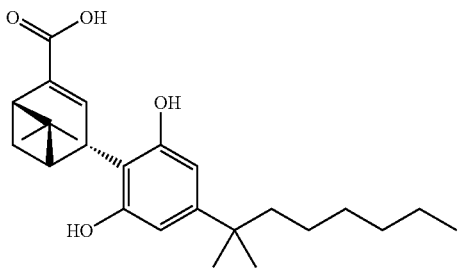
(XII)

To a well stirred solution of compound XI (3.13 g, 5 mmol) in THF (50 mL), was added in one portion tetra-butyl ammonium fluoride (5.24 g, 20 mmol). The reaction mixture was stirred at room temperature for 30 min, diluted with 100 mL of ether, washed with water (5×150 ml), dried (Na$_2$SO$_4$), filtered, and evaporated under reduced pressure to afford 2.74 g of (XII).

Example 10

Synthesis of (+)-(1-a-H,4-P-H,5-a-H-4-[2.6-di-acetylmethyloxy-4-(1,1-dimethylheptyl)phenylj-6,6-dimethylbicyclo[3.1.1]hept-2-ene-2-carboxylic Acid (XIII)

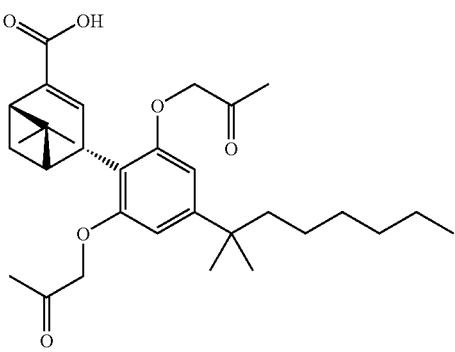
(XIII)

To a suspension of compound XII (0.109 g, 0.25 mmol) and potassium carbonate (0.138 g, 1 mmol) in anhydrous acetone (4 mL) was added chloroacetone (60 microliters, 0.75 mmol). The reaction mixture was stirred at reflux and a catalytic amount of potassium iodide was added. After 3 hours, the solids were removed by filtration and washed with dichloromethane. The dichloromethane solvent was combined with the acetone filtrate and the combined solvents removed by evaporation. The resulting residue was purified on a reverse phase C-18 column using 70% acetonitrile (30% water, 0.1% acetic acid) to afford 86 mg of pure (XIII) (67% yield).

Example 11

Synthesis of +) (1-a-H,4-(3-H,5-a-H)-4-12.6-di(methyl acetateoxy)-4-(1,1 dimethylheptyl)phenyl]-6,6-dimethylbicyclo[3.1.1]hept-2-ene-2-carboxylic Acid (XIV)

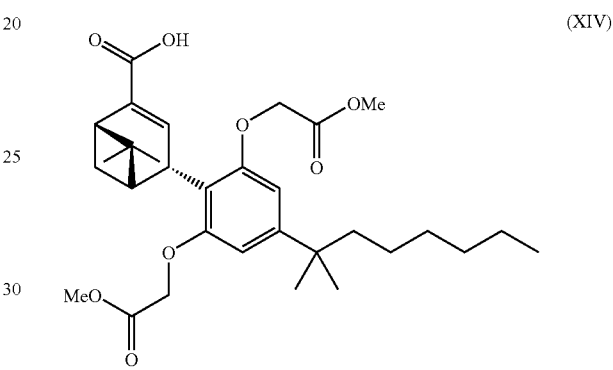
(XIV)

To a well stirred suspension of compound XIII (0.12 g, 0.3 mmol) and potassium carbonate anhydrous (0.18 g, 1.3 mmol) in dry acetone (10 ml) was added methyl bromoacetate (95 microliters, 1 mmol). The reaction mixture was stirred under reflux for 4 hours and then allowed to stir at room temperature overnight. HPLC analysis showed 2 products, the mono and dialkylated products. An additional amount of methyl bromoacetate (95 microliters, 1 mmol) was added and reflux was continued for another 3 hours. HPLC analysis showed a single peak corresponding to the dialkylated product. The solids were removed by filtration and washed with dichloromethane. The dichloromethane solvent was combined with the acetone filtrate and the combined solvents removed. The resulting residue was dissolved in ethyl acetate (10 ml), the organic solution washed with water, dried (Na$_2$SO$_4$), filtered, and evaporated to afford 0.12 g of pure (XIV) (78% yield).

Example 12

Effects of HU-308 on Animals—Animals and Administration of Drugs

Female Sabra mice (2 months old, Harlan-Sprague Dawley, Jerusalem) were used for a series of tests for psychotropic effects (the "tetrad"), for assessing intestinal immotility ("defecation"), and for the assays for inflammation and peripheral pain. Blood pressure was measured in male Sabra rats. HU-308, SR 141716A and SR 144528 (the latter two were a generous gift of Sanofi Reserche, France) were dissolved in a vehicle of ethanol: emulphor:saline (1:1:18) [Martin, B. R., Compton, D. R., Thomas, B. F., Prescott, W. R., Little, P. J., Razdan, R. K., Johnson, M R., Melvin, L. S., Mechoulam, R. & Ward, S. J. (1991) Pharmacol. Biochem. Behavior, 40,471–478 and Fride, E. & Mechoulam, R. (1993) Eur. J. Pharmacol. 231, 313–314] and injected in volumes of 0.1 ml/10 in mice or 0.1 ml/100 g in rats. HU-308 was administered intrapentoneally (i.p.) into mice in the behavioral, the anti-inflammatory, and the antinociceptive assays. In experiments where blood pressure was monitored it was administered i.v. into rats.

Receptor Binding Assays

The CB1 binding assays were performed with synaptosomal membranes prepared from rat brains [Devane, W. A., Hanus, L., Breuer, A., Pertwee, R. G., Stevenson, L. A., Griffin, G., Gibson, D., Mandelbaum, A., Etinger, A., & Mechoulam, R. (1992) Science 258, 1946–1949]. The CB2 assays were performed with transfected cells [Mechoulam, R., Ben-Shabat, S., Hanus, L., Ligumsky, M., Kaminski, N. E., Schatz, A. R., Gopher, A., Almog, S., Martin, B. R., Compton, D. R., Pertwee, R. G., Griffin, G., Bayewitch, M., Barg, J. & Vogel, Z. (1995) Biochem. Pharmacol. 50, 83–90]. The previously described probe [$_3$H]HU-243 was employed in a centrifugation based ligand binding assay [Devane, W. A., Hanus, L., Breuer, A., Pertwee, R. G., Stevenson, L. A., Griffin, G., Gibson, D., Mandelbaum, A., Etinger, A., & Mechoulam, R. (1992) Science 258, 1946–1949 and Devane, W. A., Breuer, A., Sheskin, T., Jarbe, T. U. C., Eisen, M. & Mechoulam, R. (1992) J. Med. Chem. 35, 2065–2069].

Pharmacological Assays in Mice

A series of four consecutive observations are performed on each mouse following a standard procedure employed to evaluate psychoactive cannabinoid-induced effects in mice [Martin, B. R., Compton, D. R., Thomas, B. F., Prescott, W. R., Little, P. J., Razdan, R. K., Johnson, M. R., Melvin, L. S., Mechoulam, R. & Ward, S. J. (1991) Pharmacol. Biochem. Behavior, 40, 471–478] using time intervals similar to those previously described [Fride, E. & Mechoulam. R. (1993) Eur. J. Pharmacol. 231, 313–314]. At various times after injection mice were tested in four assays consecutively. The four assays were (1) motor activity (ambulation and rearing) in an open field (20×30 cm, divided into 12 squares of equal size) for 8 min; (2) immobility ("catalepsy") on a ring of 5.5 cm diameter for 4 min; (3) body temperature with a telethermometer (Yellow Springs Instruments Co.); and (4) analgesia on a hot plate maintained at 55° C., measured as the latency (in seconds) until the first hind paw lick or jump from the plate (the latter response was rarely observed) with a maximum of 45 s. The results of this study are provided in FIG. 3 in graphical form.

Inhibition of Intestinal Motility

Intestinal motility was measured by injecting the mice with HU-308 (20, 50 or 100 mg/kg) and immediately after injection separating the mice into individual cages and recording the number of fecal pellets every 15 min for 2 hours. Rectal temperature was also recorded as a measure of central activity. The results of this study are provided in FIG. 4 in graphical form.

Arachidonic Acid-Induced Ear Inflammation in the Mouse

Ear inflammation was measured by assessing ear tissue swelling after topical application of arachidonic acid. Non-steroidal anti-inflammatory drugs have been shown to reduce swelling in this model [Young, J. M., Spires, D. A., Bedord, C. J., Wagner, B., Ballaron, S. & De Young, L. M. (1984) J. Invest. Dernlatol. 82, 367–371]. At various times after i.p. injections of HU-308 (50 mg/kg), arachidonic acid was applied to the inner surface of one ear (4.5 mg in 5 ml ethanol). The opposite ear served as a control (5 ml ethanol). Ear thickness was determined (in 0.01 mm units) every 15 min for 90 min starting immediately after arachidonic acid application using a dial thickness gauge (Mitutoyo, Japan). The results of this study are provided in FIG. 6 in graphical form.

Peripheral Pain

Pain mediated by the peripheral nervous system, was tested in the "formalin test" for cutaneous (peripheral) pain [Tjolson, A., Berge, O-G., Hunskaar, S., Rosland, J. H. and Hole, K. (1992) Pain, 51, 5–17; Calignano, A., La Rana, G., Giuffrida, A & Piomelli, D. (1998) Nature (London) 394, 277–280; and Jagger, S. I., Hasnie, F. S., Sellaturay, S. and Rice, A.S.C. (1998) Pain 76, 189–199]. HU-308 (or vehicle) was injected i.p. In experiments which involved an antagonist, the antagonist was administered i.p. 15 min before 30 HU-308. Formalin was injected s.c. in the hind paw of a mouse 90 min after HU-308 injection. Immediately after formalin administration pain was assessed every 5 min for 1 hr by the number of times the animal licks the formalin-injected paw. The results of this study are provided in FIG. 7 in graphical form.

Blood Pressure Assay

Systemic blood pressure was monitored in male rats (Sabra strain, 270–350 g). A chronic cannula (P 50, Clay Adams) was implanted into the femoral artery under pentobarbital anesthesia (60 mg/kg). The jugular vein was cannulated for drug administration. The arterial cannula was attached to a pressure transducer (Db23, Statham City) and the transducer was connected to a data acquisition system (CODAS software and scroller card, Dataq, Ohio). Pressure was sampled at a rate of 1/s.

Recordings were taken for 30–60 min before treatment. Preliminary observations indicated that the effects of HU-308 on blood pressure returned to normal well within a 30 min period after administration. Hence, measurements were performed for 30 min following i.v. bolus injections of HU-308. Only one dose of HU-308 (5–40 mg/kg) with, or without, antagonist (SR 141716A to block CB1 receptors; SR 144528 to block CB2 receptors) was administered to each rat. The results of this study are provided in FIG. 5 in graphical form.

Statistical Analyses

Time curves were compared by two-way analyses-of-variance (ANOVA: time versus dose). Differences from vehicle treatments were compared by one-way ANOVA's, followed by post-hoc Newman-Keuls tests (Prism software from Graphpad, San Diego).

Example 13

Activity of HU-308 in Acetic Acid Induced Inflammatory Bowel Disease

The activity of HU-308 at reducing acetic acid induced inflammatory bowel disease (IBD) was evaluated. Male Sprague Dawley rats (10 weeks old, 200–250 g were lightly anesthetized with ketamine rompun combination. A polyethylene catheter (outer diameter 1.7 mm) was inserted through the rectum 5 cm into the colon and 2 mL of 5% acetic acid solution was slowly administered into the colon. Fifteen seconds later the colon was washed with 3 mL of saline followed by another 3 mL of saline 15 sec later. Immediately after, animals were treated with either HU-308 (10 or 20 mg/kg) or its vehicle (2 mL/kg). The HU-308 or its vehicle were prepared by diluting 0.3 mL of either HU-308 or its vehicle with 2.7 mL of saline. The HU-308 or its vehicle was administered i.p. and was administered daily for 7 days.

Animals were clinically followed for 1 week and body weight, presence of blood in the stool, and stool consistency were monitored and recorded daily and scored on a scale of 0–4 according to the scale provided in Table 1 [Murthy et al., Dig. Dis. Sci., 38(9), 1722–1734, (1993)].

TABLE 1

Criteria for Scoring the Disease Activity Index of Inflammatory Bowel Disease (DAI).[1]

| Score | Percent Weight Loss | Stool Consistency[2] | Occult Blood or Gross Bleeding |
|---|---|---|---|
| 0 | None | Normal | Negative |
| 1 | 1–5 | Loose Stool | Negative |
| 2 | 5–10 | Loose Stool | Hemoccult Positive |
| 3 | 10–15 | Diarrhea | Hemoccult Positive |
| 4 | .15 | Diarrhea | Gross Bleeding |

[1]Disease Activity Index = (combined score of weight losss, stool consistency and bleeding)/3
[2]Normal Stool = well formed pellets; loose stool = pasty stool that does not stick to the anus; and diarrhea = liquid stool that sticks to the anus Seven days post disease induction animals were euthanized with phenobarbital (100 mg/kg i.p.), the whole colon excised, slit longitudinally, and examined under a magnifying glass. Any visible damage to the colon was recorded and scored. The scoring scale for colon damage is provided in Table 2.

TABLE 2

Gross Pathology Scoring Method for Evaluating the Severity of Inflammatory Bowel Disease.

| Score | Pathology |
|---|---|
| 0 | No damage |
| 1 | Localized hyperimia and/or edema |
| 2 | Two or more sites of hyperimia and/or edema |
| 3 | Localized erosion |
| 4 | Localized ulcer |
| 5 | More than one site of erosion or ulcer, or 1 site of ulcer extending >2 cm along the length of the colon |

Clinical outcome was analyzed using analysis of variance (ANOVA) followed by Duncan's post hoc test. A non-parametric test (Wilcox Rank Sum Test) was used to evaluate the gross pathology findings.

Figure 8:
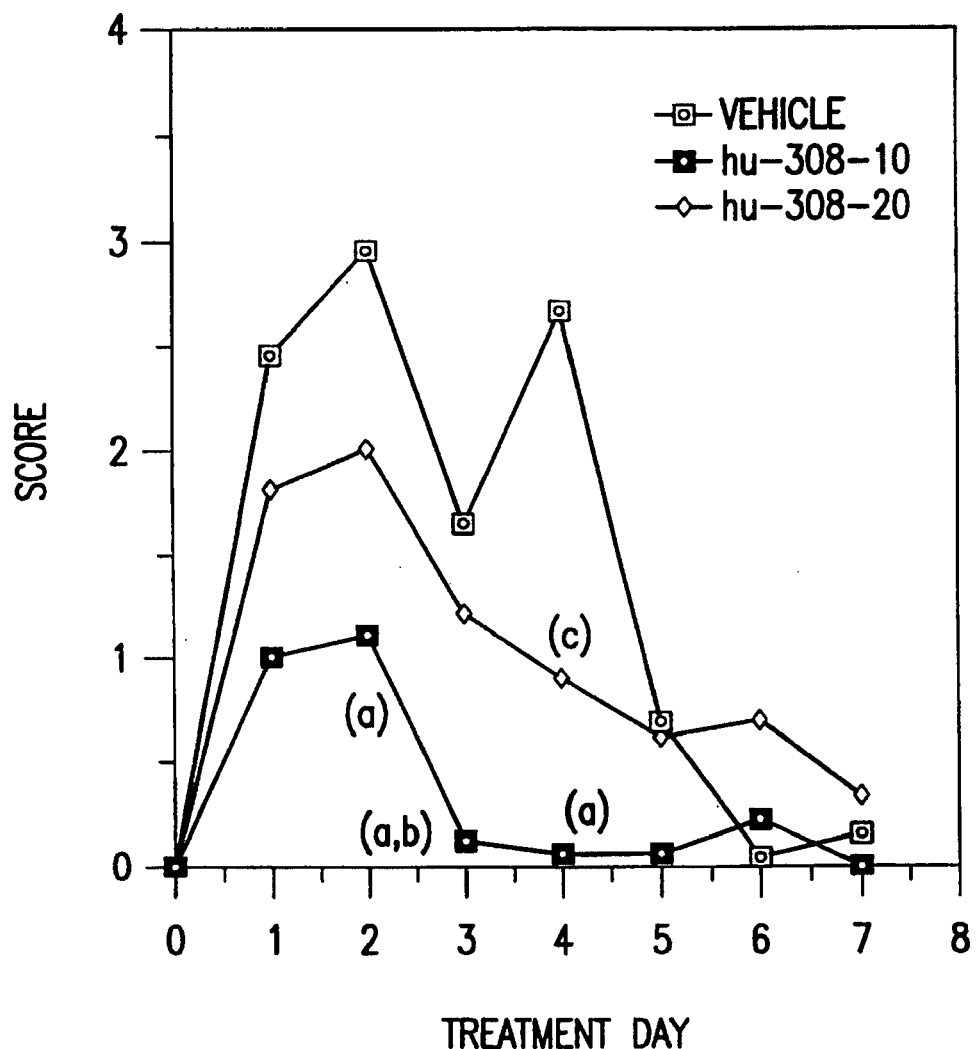
FIG. 8 is a graph of disease activity index score vs. treatment day, for mice with acid induced inflammatory bowel disease treated with 10 or 20 mg/kg of HU-308 or vehicle.

FIG. 8 shows that disease development, as indicated by disease activity index (DAI), peaked on day 3–4 and that HU-308 (10 mg/kg) reduced disease severity and increased healing compared to its vehicle and HTJ-308 (20 mg/kg). In FIG. 8 line "a" depicts HU-308 (10 mg/kg) vs. vehicle, p<0.05; line "b" depicts HU-308 (10 mg/kg) vs. HU-308 (20 mg/kg), p<0.05; and line "c" depicts HU-308 (20 mg/kg) vs. vehicle, p<0.05. The differences were statistically significant (p<0.05) on days 2, 3, and 4.

Figure 9:
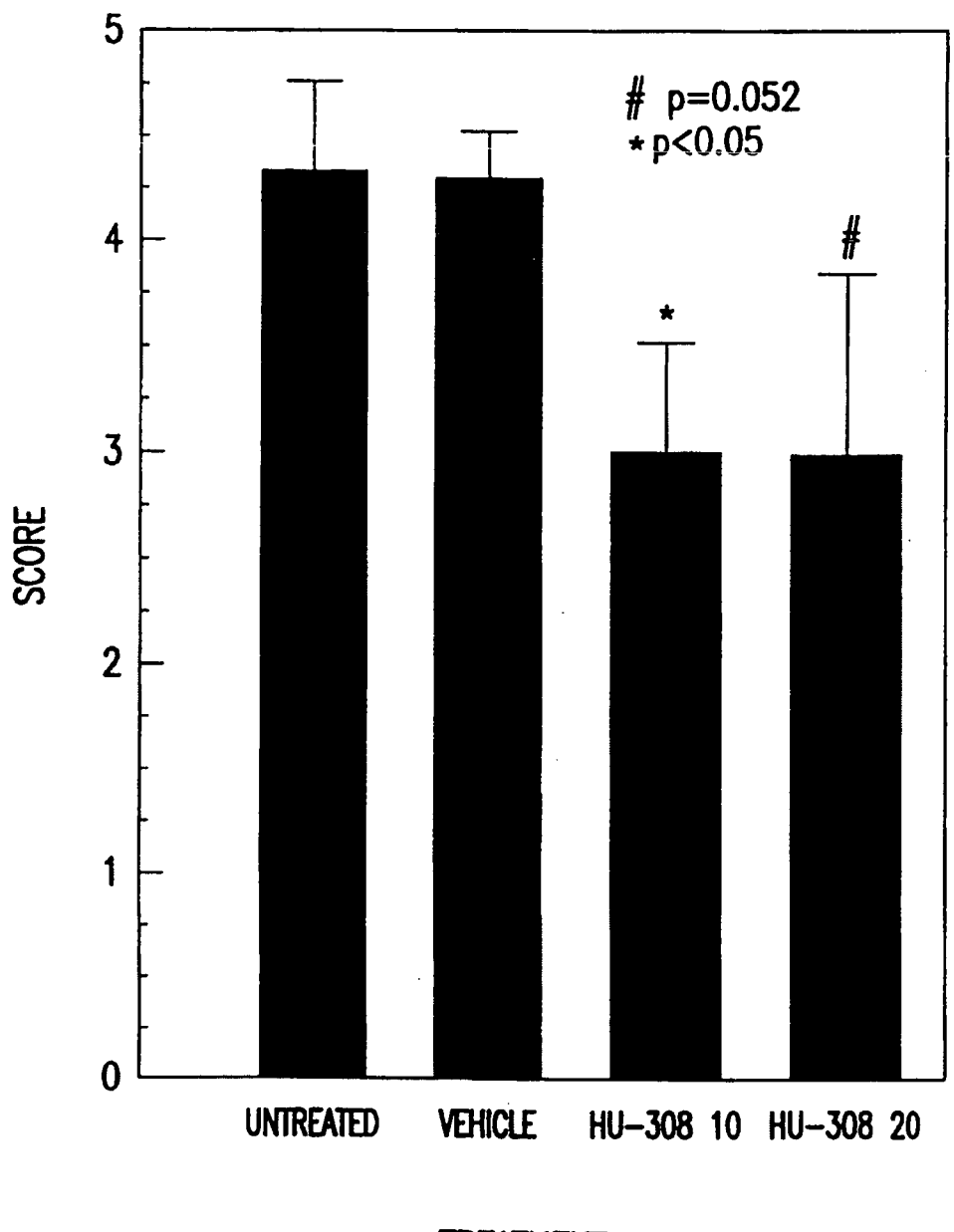
FIG. 9 is a bar graph of gross pathology score for untreated mice, mice 5 treated with vehicle, mice treated with 10 mg/kg of HU-308, and mice treated with 20 mg/kg of HU-308 after induction of acid induced inflammatory bowel disease.

FIG. 9 is a bar graph of gross pathology score (Table 2) for untreated mice, mice treated with vehicle, mice treated with 10 mg/kg of HU-308, and mice treated with 20 mg/kg of HU-308. FIG. 9 shows that HU-308 reduced the pathological lesion severity in the gastrointestinal tract by 35 percent compared to its vehicle (p<0.05 for 10 mg/kg and p=0.052 for 20 mg/kg). The results of this study show that 10 and 20 mg/kg HU-308 administer i.p. to mice daily for seven days can reduce the severity of acid induced inflammatory bowel disease.

Example 14

Anti-Inflammatory Effect of HU-308 in Models of Autoimmune Disease

Autoimmune diseases are associated with elevated levels of inflammatory cytokines. The most convenient models for studying autoimmune disease are experimental allergic encephalomyelitis (EAE) and experimental autoimmune arthritis in rodents. EAE is an autoimmune neurological disease elicited by sensitization of the animals to myelin basic protein from the central nervous system, which is also known as basic encephalitogenic protein. EAE is considered to represent a model of the human disease multiple sclerosis. Experimental autoimmune arthritis is induced in animals by immunization with collagen in complete Freund's adjuvant. The ability of CB2 specific compounds of the general formula I to prevent or attenuate the clinical symptoms of autoimmune arthritis and EAE is evaluated.

Autoimmune Arthritis

The purpose of the study is to test the activity of HU-308 in preventing autoimmune arthritis. Experimental autoimmune arthritis is induced in animals by immunization with collagen type 2 in complete Freund's adjuvant.

Adult CD-1 male mice (27–33 gr), at least five per treatment group, are used in the study. Each animal is administered 100 μg/ml collagen type 2 in 0.1 mL complete Freund's adjuvant. The collagen is administered subcutaneously into the base of the tail. The volume of each hind paw is measured using a plethysmometer (commercially available from Hugo Basill of Italy) before collagen administration and on days 1, 4, 7, 10, 13, and 16 of treatment (30 minutes after drug treatment). The following treatment groups are tested: vehicle (blank cosolvent using a standard volume of 10 ml/kg) alone, HU-308 at doses of 2–15 mg/kg every three days, HU-308 at doses of 2–15 mg/kg once daily, and diclofenac 10 mg/kg (10 ml/kg) every 3 days, as a positive control. All treatments are administered intraperitoneally. HU-308 is used from a 5% stock preparation in cosolvent by diluting with saline 1:25. The same procedure is performed with blank cosolvent. Diclofenac is prepared at Pharmos, as a solution of 1 mg/ml. At the same time the paws are measured they are also clinically evaluated according to the method of R. O Williams, Proc. Natl. Acad. Sci. USA: 89: 9784–9788, wherein 0=normal, 1=slight swelling and erythema, 2=pronounced edematous swelling, and 3=joint rigidity. On day fifteen of treatment the animals are euthanised with pentobarbital 100 mg/kg i.p. Blood samples (in heparin) are taken to determine hematocrit levels and blood levels of HU-308.

The major arthritis related sign that is evident in experimental autoimmune arthritis is swelling of the paws. Animals treated with HU-308 demonstrate a decreased incidence and severity of swelling of the paws, compared to the other treatment groups. The differences are compared using a non parametric analysis (Wilcoxon Rank Sum Test). The diclofenac treated animals demonstrate a smaller paw volume compared to the vehicle treated rats, but this difference is not statistically significant.

Attentuation of Experimental Autoimmune Encephalomyelitis EAE)

Various systems for induction of autoimmune encephalomyelitis are known in the art, depending on the strain of animal and the antigen employed to indue the disease. EAE is tested using Lewis rats in which the disease displays onset of symptoms around day 10 after induction and spontaneous recovery around 18 days after induction of the disease. The animals (at least 5 per test group) are maintained on a 12 hour light/12 hour dark regimen, at a constant temperature of 22° C., with food and water ad libitum. EAE is induced in the animals by immunization with purified guinea pig myelin basic protein emulsified in Complete Freund's Adjuvant. Guinea pig myelin basic protein (mbp) is prepared from spinal cord homogenates defatted with chloroform/ethanol and the isolated protein is purified using ion exchange chromatography. Each animal receives 50 micrograms of the purified protein. A solution of mbp (0.5 mg/ml) is emulsified with an equal volume of Complete Freund's Adjuvant containing 4 mg/ml of mycobacterium tuberculosis, and each animal receives 100 microliters (50 µl in each hind foot pad).

Animals are treated with HU-308 or vehicle control administered intravenously in a volume of 2 ml. The time of treatment varies from day 10 to day 18 post induction of disease, with at least five animals per group. The results show diminution of mean clinical score in HU-308 treated animals according to the following scale: 1 indicates tail paralysis, 2 indicates paraplegia, 3 indicates quadriplegia, 4 indicates complete body paralysis, and 5 indicates death.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method of treating a disease or disorder that is mediated by peripheral cannabinoid receptors CB2 in an animal, which comprises administering to an animal in need of such treatment a pharmaceutical composition that includes a therapeutically effective amount of a C2 agonist that binds to such receptors to treat the disease or disorder, wherein the CB2 agonist is a compound of the general formula:

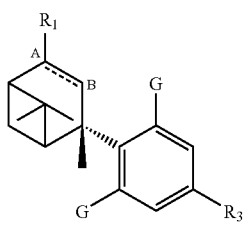

having the (3S,4S) configuration, and which is essentially free of the (3R,4R) enantiomer, wherein:
A—B designates an optional double bond,
$R_1$ is (a) —R'N(R")$_2$ wherein R' is $C_1$–$C_5$ straight or branched chain alkyl and each R", which may be the same or different, is hydrogen or $C_1$–$C_5$ straight or branched chain alkyl optionally containing a terminal —OR''' or —OC(O)R''' moiety wherein R''' is hydrogen or $C_1$–$C_5$ straight or branched chain alkyl, (b) —Q wherein Q is a heterocyclic moiety having a labile hydrogen atom so that said moiety acts as a carboxylic acid analogue, (c) —R'X wherein R' is $C_1$–$C_5$ straight or branched chain alkyl and X is halogen, (d) —R'C(O)N(R")$_2$ wherein R' is a direct bond or $C_1$–C5 straight or branched chain alkyl and each R''', which may be the same or different, is hydrogen or $C_1$–$C_5$ straight or branched chain alkyl optionally containing a terminal —OR''' or —OC(O)R''' moiety wherein R''' is hydrogen or $C_1$–$C_5$ straight or branched chain alkyl, (e) —R'C(O)OR" wherein R' is a direct bond or $C_1$–$C_5$ straight or branched chain alkyl and R" is hydrogen or $C_1$–$C_5$ straight or branched chain alkyl optionally containing a terminal —OR''' or —OC(O)R''' moiety wherein R''' is hydrogen or $C_1$–$C_5$ straight or branched chain alkyl, (f) —R' wherein R' is $C_1$–$C_5$ straight or branched chain alkyl, or (g) —R'OR''' wherein R' is $C_1$–$C_5$ straight or branched chain alkyl and R''' is hydrogen or $C_1$–$C_5$ alkyl;

G is hydrogen, halogen, or —OR$_2$ wherein R$_2$ is hydrogen or $C_1$–$C_5$ alkyl optionally containing a terminal —OR''', —OC(O)R''', —C(O)OR''', or —C(O)R''' moiety wherein R''' is hydrogen or $C_1$–$C_5$ alkyl; and $R_3$ is (a) $C_1$–$C_{12}$ straight or branched chain alkyl, (b) —OR'''', in which R'''' is a straight chain or branched $C_2$–$C_9$ alkyl which may be substituted at the terminal carbon atom by a phenyl group, or (c) —(CH$_2$)$_n$OR''' wherein n is an integer of 1 to 7 and R''' is hydrogen or $C_1$–$C_5$ alkyl, wherein the disease or disorder to be treated is hypertension, gastrointestinal disorders, tumors expressing CB2 receptors or autoimmune diseases and the pharmaceutical composition is administered to an individual in a therapeutically effective amount for treating the disease or disorder.

2. The method of claim 1, wherein the method is for preventing, treating, or managing tumors expressing CB2 receptors.

3. The method of claim 1, wherein the method is for preventing, treating, or managing hypertension.

4. The method of claim 1, wherein the method is for preventing, treating, or managing autoimmune diseases.

5. The method of claim 1, wherein G is —OCH$_3$ and R$_3$ is 1,1-dimethyl heptyl.

6. The method of claim 1, wherein R$_1$ is —CH$_2$OH, G is —OCR$_3$, and R$_3$ is 1,1-dimethyl heptyl.

7. The method of claim 1, wherein the pharmaceutical composition further comprises a pharmaceutically acceptable diluent that is an aqueous cosolvent solution.

8. The method of claim 7, wherein the diluent comprises a pharmaceutically acceptable cosolvent, a micellar or emulsion solution prepared with natural or synthetic ionic or nonionic surfactants, or a combination of such cosolvent and micellar or emulsion solutions.

9. The method of claim 1, wherein the pharmaceutical composition further comprises a pharmaceutically acceptable carrier.

10. The method of claim 9, wherein the carrier comprises a solution of ethanol, a surfactant and water or an emulsion comprising triglycerides, lecithin, glycerol, an emulsifier, an antioxidant and water.

11. The method of claim 1, wherein A—B designates a double bond, R$_1$ is —CH$_2$OH, G is —OCH$_3$, and R$_3$ is 1,1-dimethyl heptyl.

* * * * *

UNITED STATES PATENT AND TRADEMARK OFFICE
CERTIFICATE OF CORRECTION

| | | |
|---|---|---|
| PATENT NO. | : 7,214,716 B2 | Page 1 of 1 |
| APPLICATION NO. | : 11/043089 | |
| DATED | : May 8, 2007 | |
| INVENTOR(S) | : Fride | |

It is certified that error appears in the above-identified patent and that said Letters Patent is hereby corrected as shown below:

Column 19:
Line 38 (claim 1, line 5), change "C2" to -- CB2 --.

Column 20:
Line 3, change "$C_1$–C5" to -- $C_1$–$C_5$ --.
Line 44 (claim 6, line 2), change "—$OCR_3$," to -- —$OCH_3$, --.

Signed and Sealed this

Fourth Day of March, 2008

JON W. DUDAS
*Director of the United States Patent and Trademark Office*

UNITED STATES PATENT AND TRADEMARK OFFICE
CERTIFICATE OF CORRECTION

PATENT NO. : 7,214,716 B2  Page 1 of 1
APPLICATION NO. : 11/043089
DATED : May 8, 2007
INVENTOR(S) : Fride It is certified that error appears in the above-identified patent and that said Letters Patent is hereby corrected as shown below:

<u>Title Page</u>:
Insert the following before Item (51) on the title page:
-- (30)   Foreign Application Priority Data
   Oct. 31, 1999   (IL) ………………….. 132661 --.

Signed and Sealed this

Fifth Day of August, 2008

JON W. DUDAS
*Director of the United States Patent and Trademark Office*